United States Patent [19]

Rothfuss et al.

[11] Patent Number: 4,605,001
[45] Date of Patent: Aug. 12, 1986

[54] SURGICAL STAPLING INSTRUMENT WITH DUAL STAPLE HEIGHT MECHANISM

[75] Inventors: Robert G. Rothfuss, Bellevue, Ky.; David K. Kuhl, Cincinnati, Ohio; Michael A. Murray, Bellevue, Ky.

[73] Assignee: Senmed, Inc., Cincinnati, Ohio

[21] Appl. No.: 662,621

[22] Filed: Oct. 19, 1984

[51] Int. Cl.$^4$ ............................................. A61B 17/11
[52] U.S. Cl. ................................. 128/305; 128/334 R; 227/19; 227/DIG. 1
[58] Field of Search ............. 128/334 R, 305; 227/19, 227/DIG. 1, 135, 152

[56] References Cited

U.S. PATENT DOCUMENTS

| | | | |
|---|---|---|---|
| D. 272,851 | 2/1984 | Green et al. | D24/26 |
| D. 272,852 | 2/1984 | Green et al. | D24/26 |
| 960,300 | 6/1910 | Fischer | 227/152 |
| 2,344,071 | 3/1944 | Wilson et al. | 227/19 |
| 3,017,637 | 1/1962 | Sampson | 227/19 X |
| 3,078,465 | 2/1963 | Bobrov | 128/334 R |
| 3,079,606 | 3/1963 | Bobrov | 227/76 |
| 3,315,863 | 4/1967 | O'Dea | 227/19 |
| 3,317,105 | 5/1967 | Astafjev et al. | 128/334 R X |
| 3,490,675 | 1/1970 | Green et al. | 227/19 |
| 3,499,591 | 3/1970 | Green | 227/76 |
| 3,551,987 | 1/1971 | Wilkinson | 128/334 R |
| 4,111,206 | 9/1978 | Vishnevsky et al. | 128/334 R X |
| 4,241,861 | 12/1980 | Fleischer | 227/135 |
| 4,244,372 | 1/1981 | Kapitanov et al. | 227/DIG. 1 X |
| 4,290,542 | 9/1981 | Fedotov et al. | 227/DIG. 1 X |
| 4,328,805 | 5/1982 | Akopov et al. | 128/334 R |
| 4,429,695 | 2/1984 | Green | 128/334 R X |
| 4,520,817 | 6/1985 | Green | 128/305 |

FOREIGN PATENT DOCUMENTS 1213583 3/1983 Australia .
599799 3/1978 U.S.S.R. ........................ 227/DIG. 1

Primary Examiner—Paul E. Shapiro
Attorney, Agent, or Firm—Charles P. Boukus, Jr.; Jerrold J. Litzinger

[57] ABSTRACT

A surgical stapling instrument suitable for performing a gastrointestinal anastomosis is provided. The stapling instrument incorporates an improved staple actuator mechanism operable by separate control buttons to accomplish its stapling and cutting actions in two stages. The two stage operation of the stapling instrument reduces the maximum force required to operate the instrument. The improved actuator mechanism permits selection of different staple heights to be produced by the same instrument. In addition, the actuator mechanism is designed to stabilize the upper and lower jaw members by providing longitudinal and lateral support along substantially the entire length of the operative portions of the jaw members. Preferably, the actuator mechanism comprises an elongated, I-beam structure slidably mounted for longitudinal movement relative to the jaw members. The I-beam assembly includes upper and lower flanges which provide both longitudinal and lateral support along substantially the entire length of the anvil and staple cartridge carrying portions of the jaw members. A sleeve slidably mounted on one of the I-beam flanges allows the spacing of the jaw members to be adjusted to produce one of two predetermined closed staple heights.

38 Claims, 17 Drawing Figures

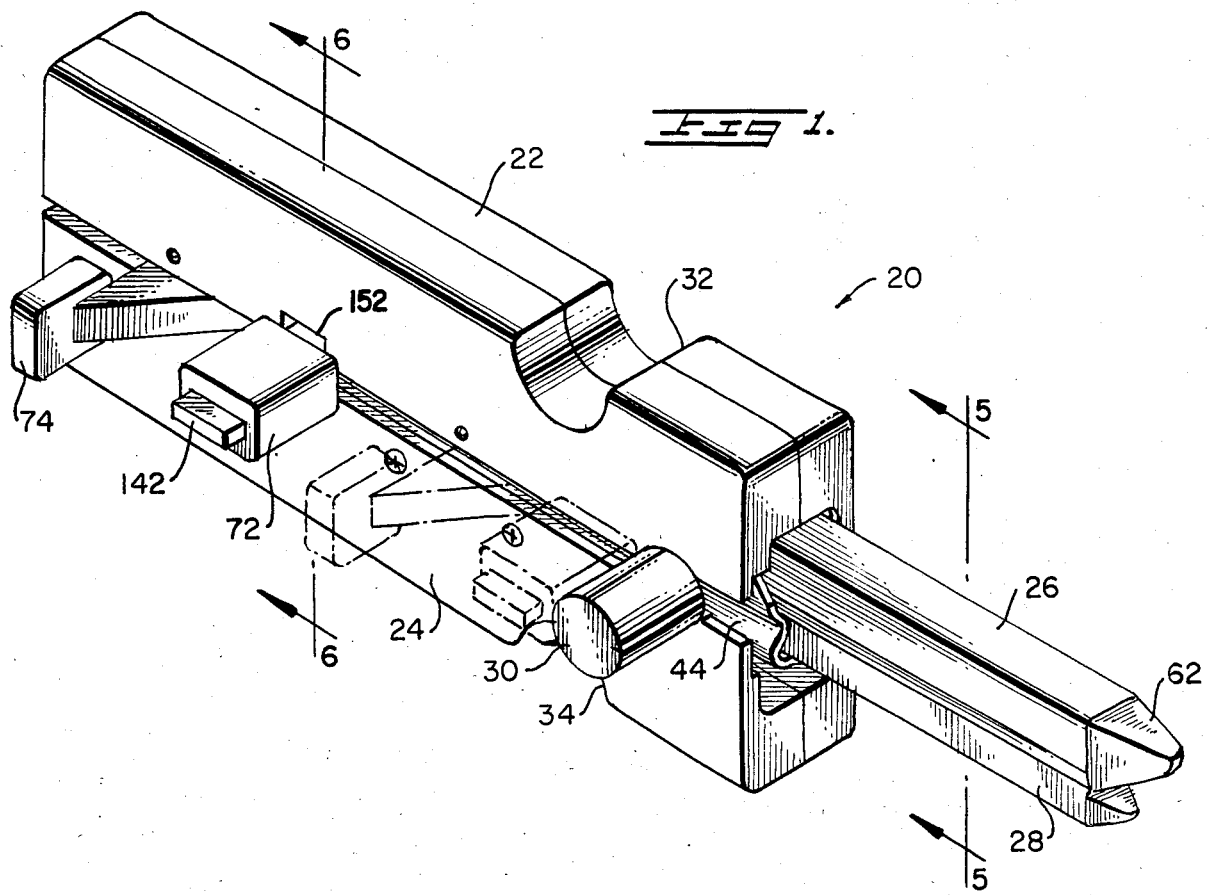
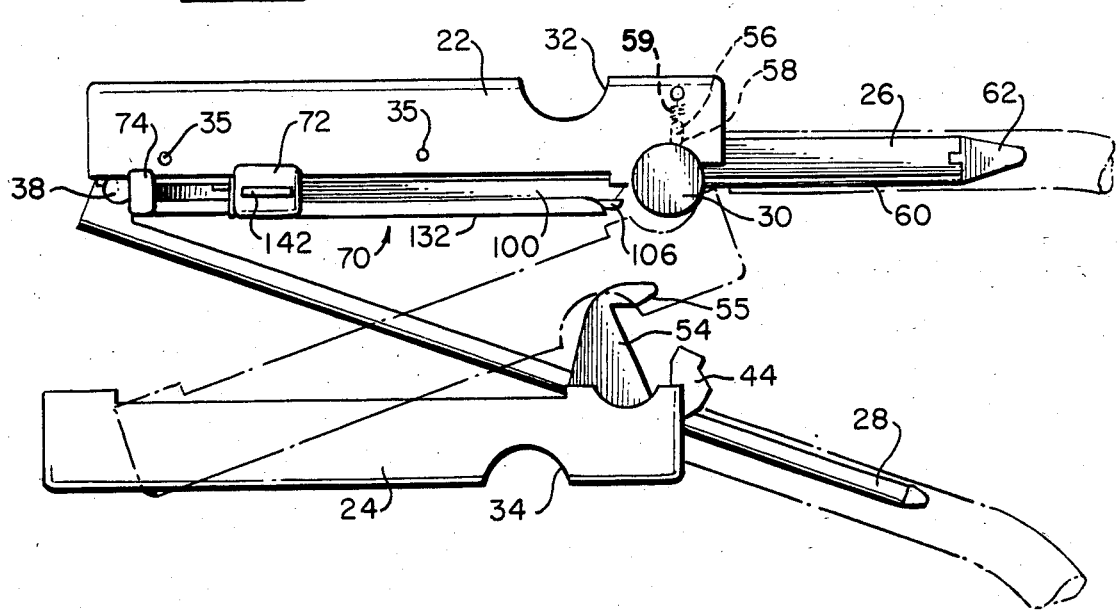

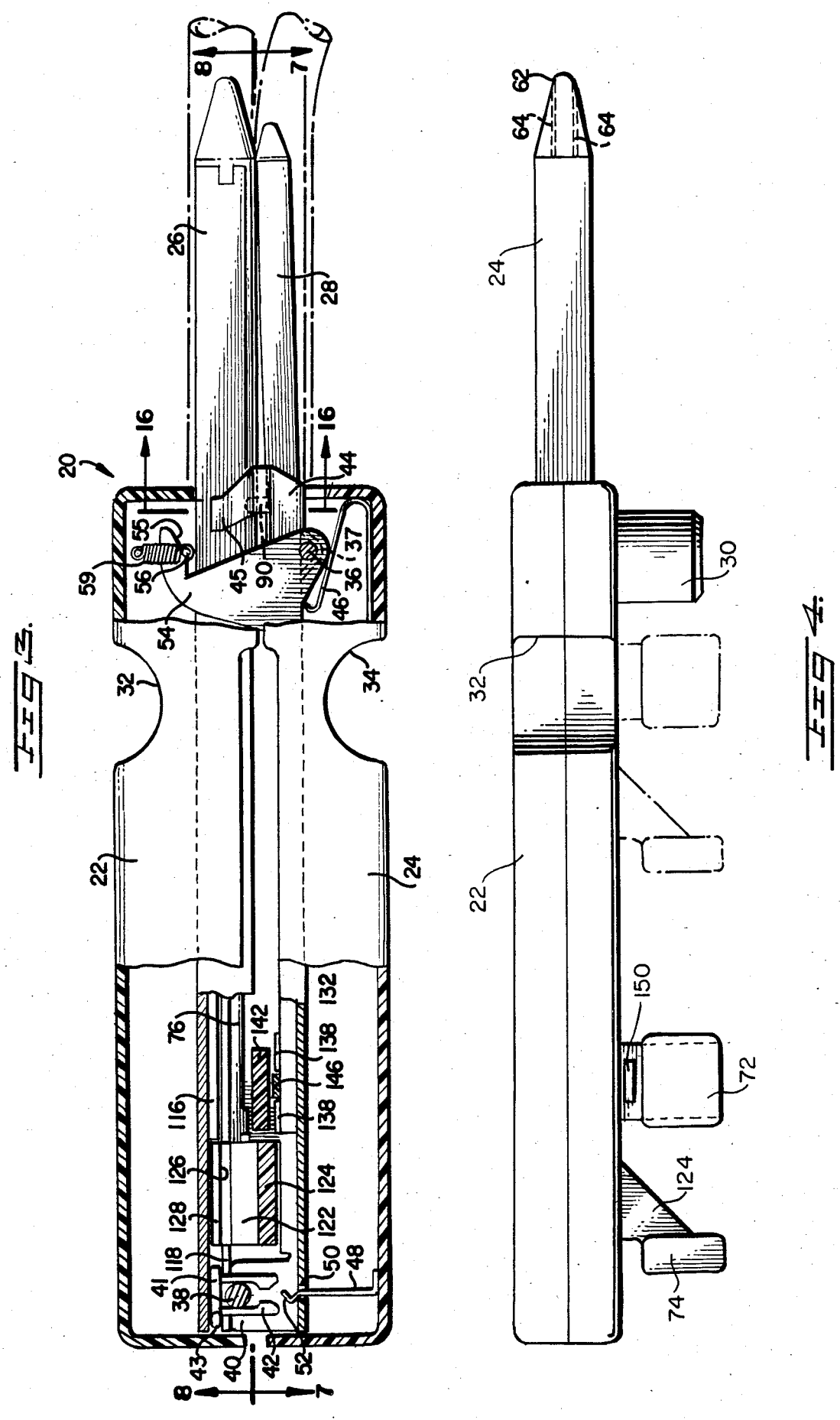

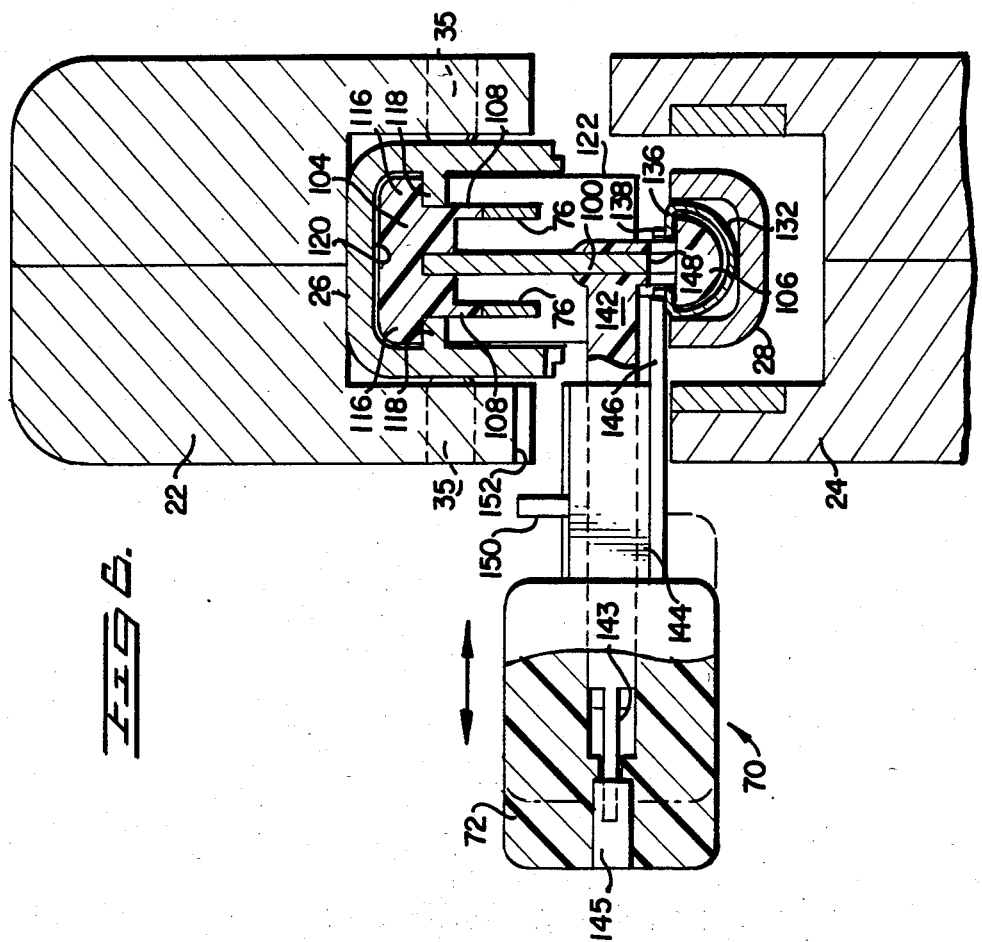
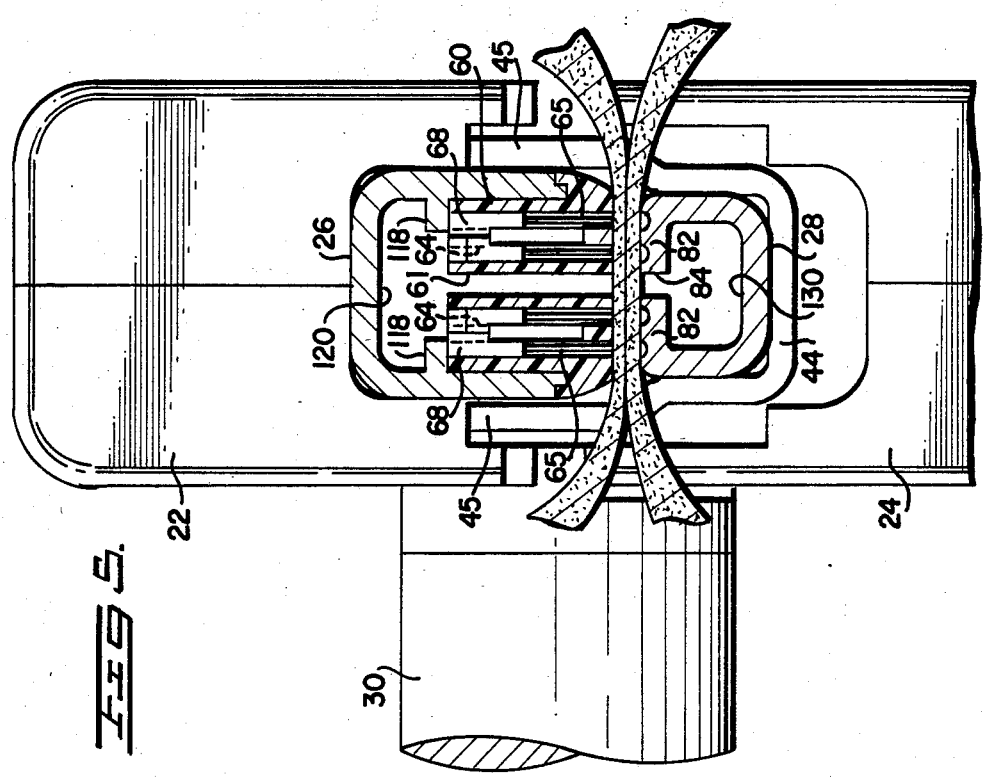

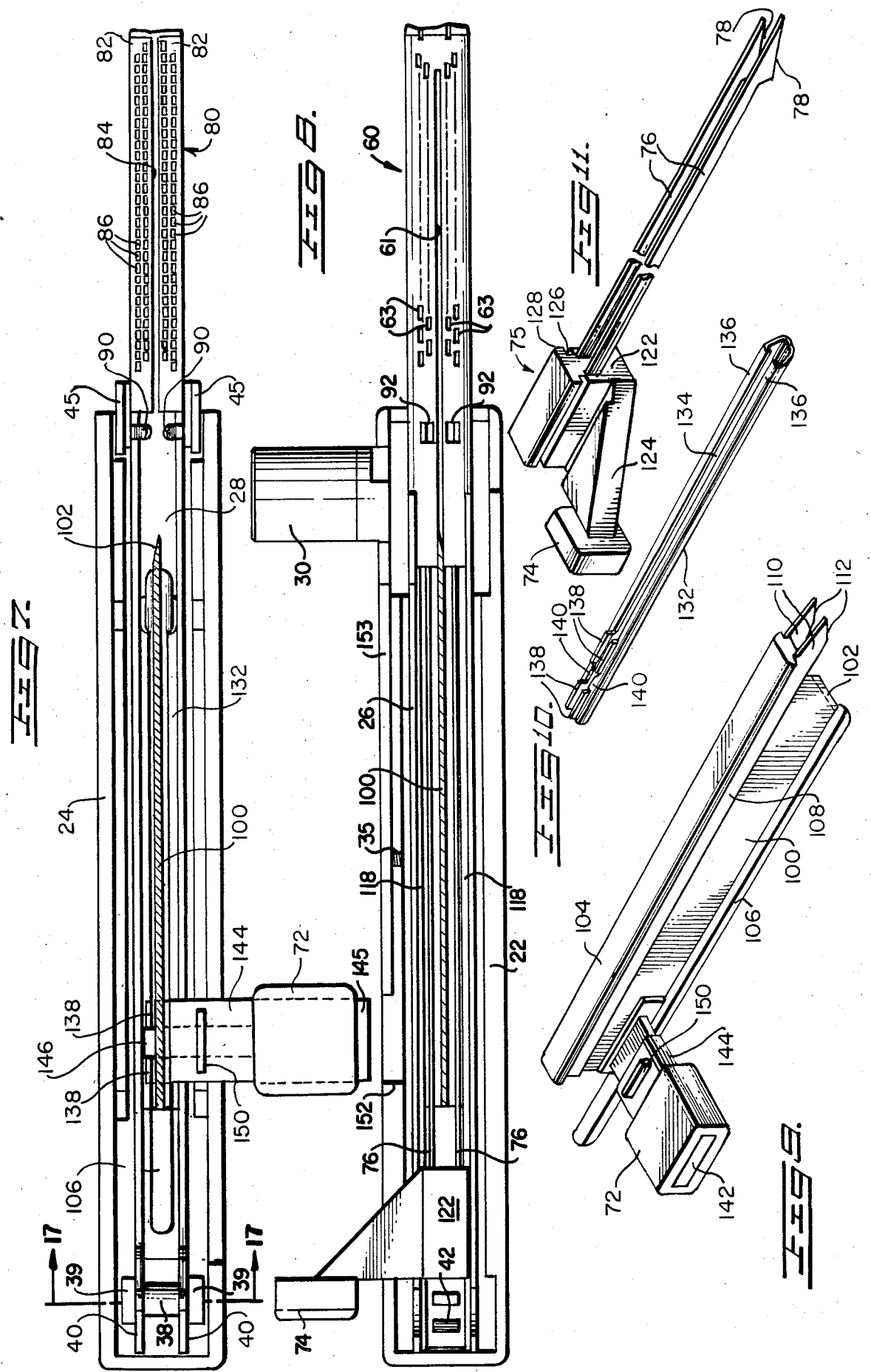

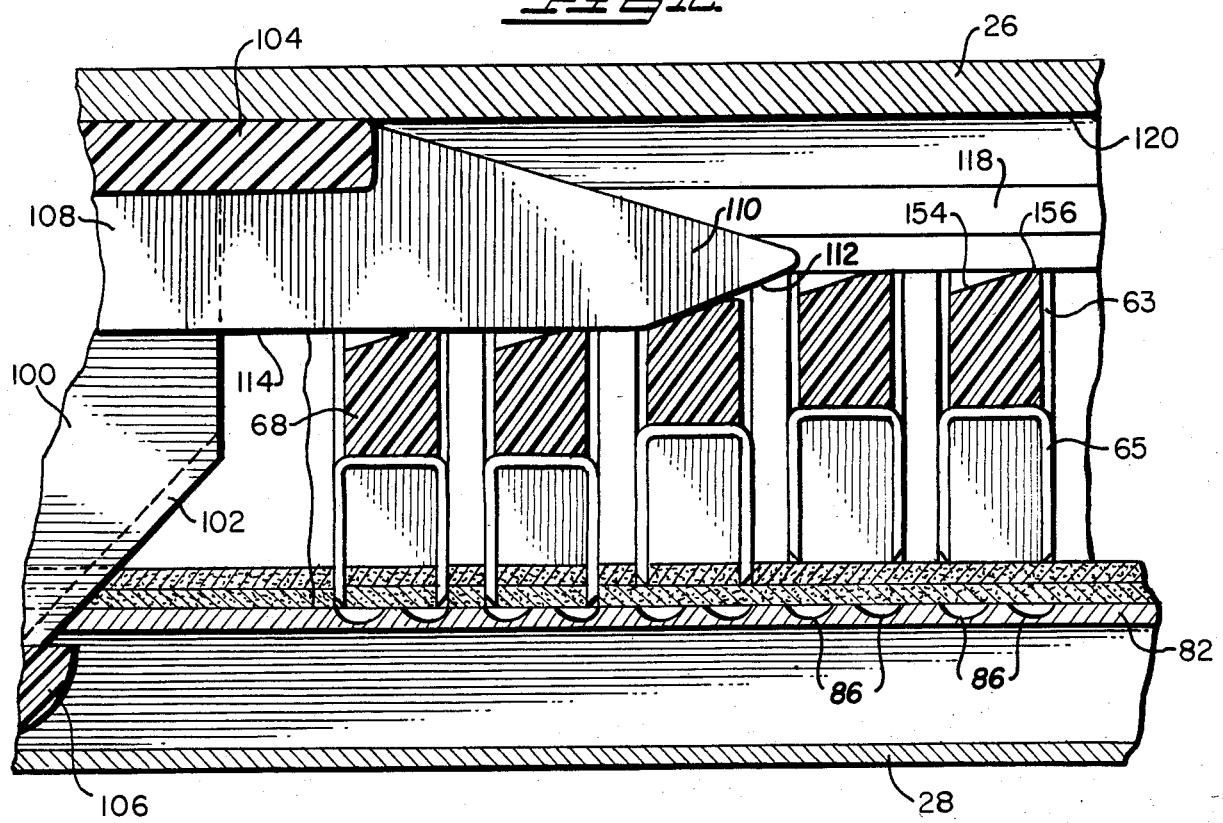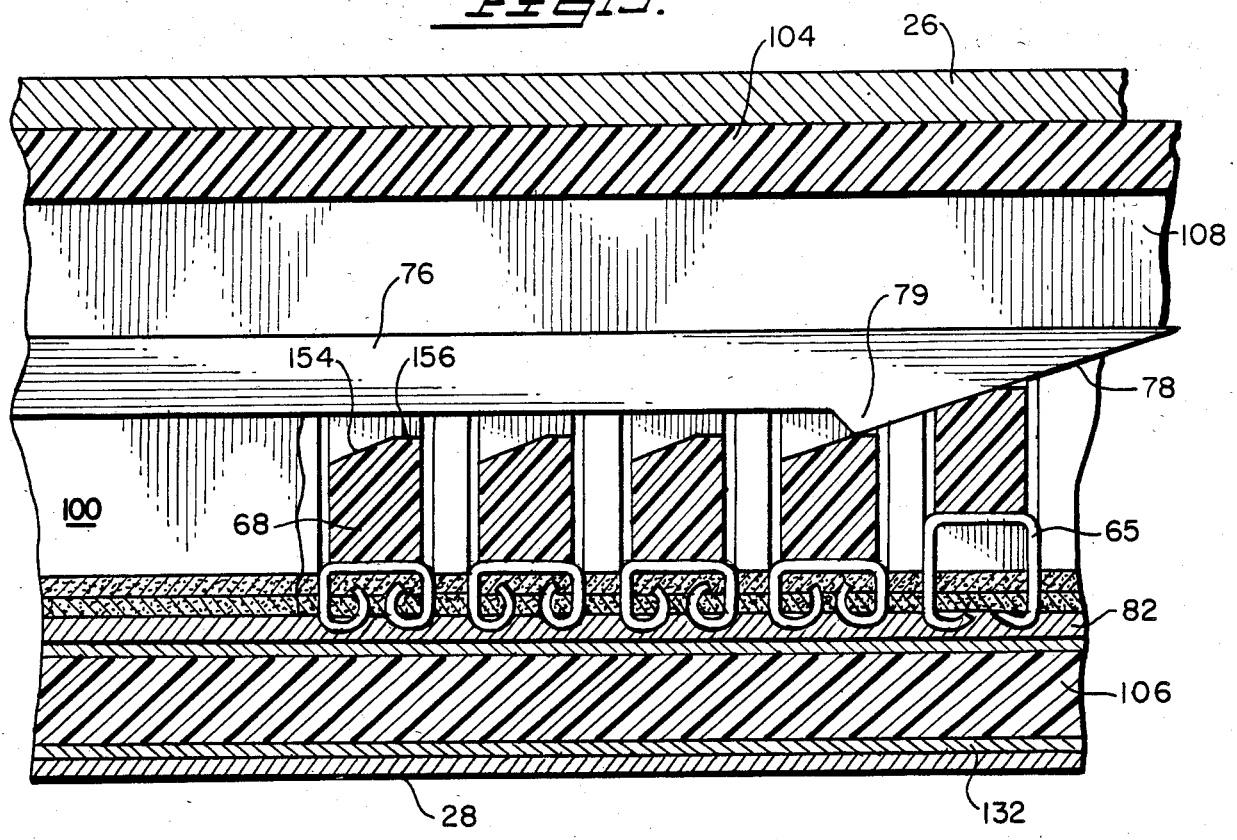

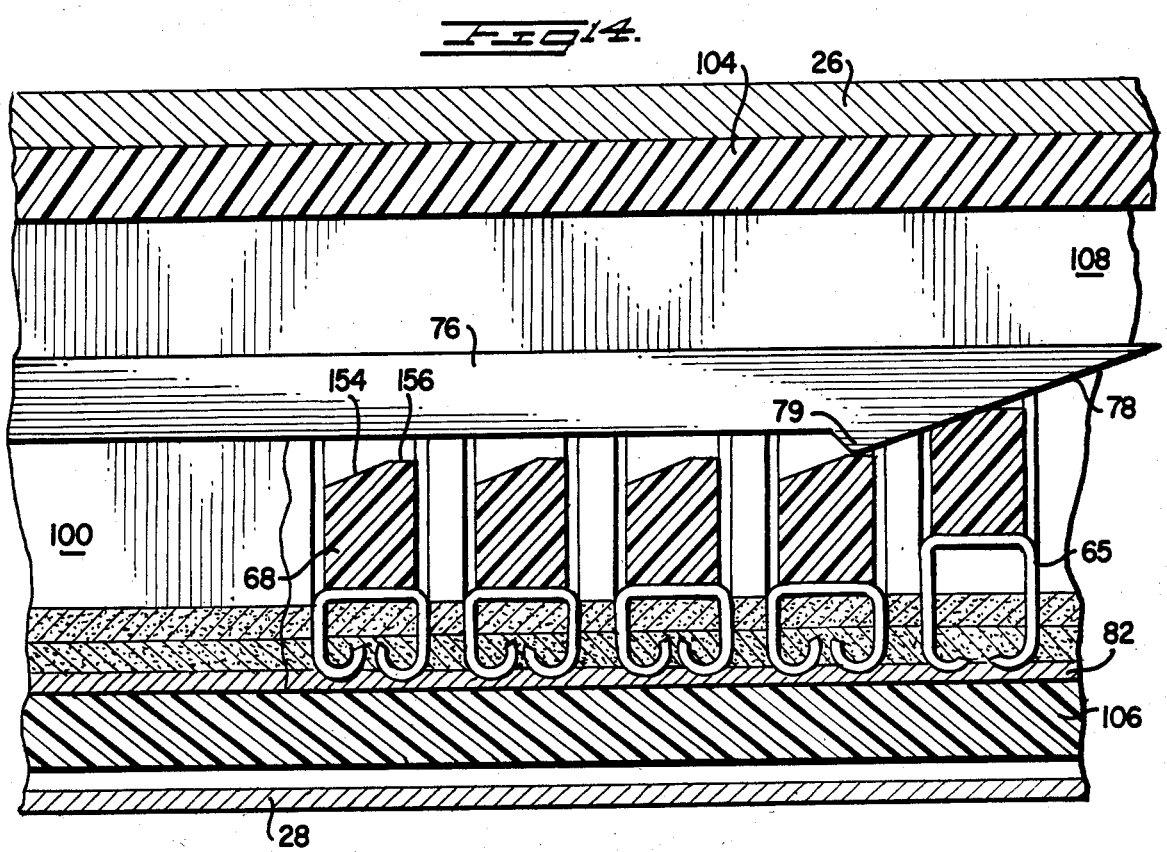
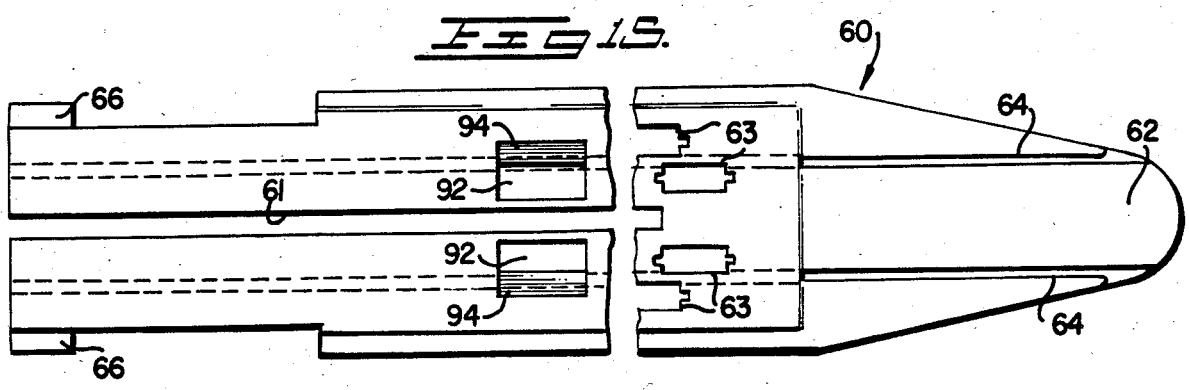
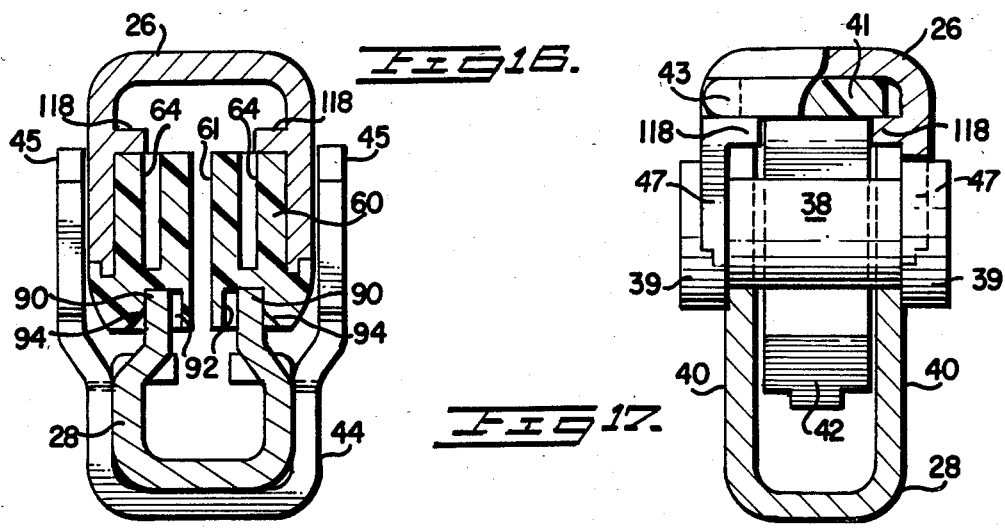

SURGICAL STAPLING INSTRUMENT WITH DUAL STAPLE HEIGHT MECHANISM

FIELD OF INVENTION

The present invention relates to a surgical stapling instrument and, more particularly, to a gastrointestinal anastomotic stapling instrument for producing one or more rows of staples which forms the staples in two stages and enables different staple heights to be selected. Specifically, this invention relates to a linear anastomotic stapling instrument including an improved staple actuator mechanism which advantageously allows one of two predetermined staple heights to be selected, which reduces the forces required to operate the stapling instrument to eject and form the staples into tissue gripped between its jaw members, and which provides support and stability along substantially the entire length of the anvil and staple cartridge carrying portions of its jaw members during the ejection and forming of the staples.

BACKGROUND AND PRIOR ART

In recent years, there has been an increasing tendency for surgeons to use stapling instruments to suture body organs and tissues such as lung, esophagus, stomach, duodenum and other body organs in the intestinal tract. The use of an appropriate stapling instrument in most instances performs a better job in less time and simplifies certain previously difficult surgical procedures such as gastrointestinal anastomoses.

In the prior art, the early linear four row cutting staplers were permanent instruments into which the staples were individually hand loaded. These staplers were very expensive, bulky, heavy and difficult to load and to clean for each surgical use. An example is disclosed in U.S. Pat. No. 3,315,105. An improvement of the permanent type surgical stapler was made by providing the basic stapling instrument with a presterilized disposable staple loading unit and with an optional knife for dividing the tissue simultaneously while forming the rows of staples. An example is disclosed in U.S. Pat. No. 3,499,591. However, this improvement mainly accomplished the saving of the time previously required to load the staples by hand. It was still necessary for the basic instrument to be disassembled, cleaned, reassembled and fitted with a new cartridge and anvil for each surgical procedure, in addition to the maintenance required of the stapling instrument itself. Another problem with this type of instrument is the tendency for the jaws to spread apart at the distal end after repeated use resulting in a substantial variation in the formed staple heights between the proximal and distal ends of the staple rows.

As hospital costs have continued to increase, it has become necessary to eliminate unnecessary work and develop more efficient techniques without compromise to the surgical procedure. Consequently, disposable stapling instruments of the type disclosed in U.S. Pat. No. 4,429,695 have been developed. In the disposable stapling instrument of this patent, an actuator and knife blade assembly provides local support to the stapler jaws in the region of the knife blade and pusher bar cams. However, this stapling instrument does not address the problem of accommodating tissue of different thicknesses. If the tissue is stapled too tightly, the blood supply is compromised and the tissue may necrose. If stapled too loosely, the tissue may hemorrhage or in the case of hollow organs such as intestine may also leak. Thus, both too tightly and too loosely formed staples can cause serious problems and complications.

Typically, a linear anastomotic stapling instrument includes a pair of cooperating elongate jaw members, each adapted to be inserted into internal, tubular body organs to be anastomosed. One of the jaw members supports a staple cartridge with at least two laterally spaced rows of staples, and the other jaw member supports an anvil with staple-forming pockets aligned with the rows of staples in the cartridge. Generally, a single pusher bar and knife assembly is slidable longitudinally along the jaw members to sequentially eject staples from the cartridge via camming surfaces which activate a plurality of staple drivers carried by the cartridge and associated with the individual staples to close the staples against the anvil and form laterally spaced rows of staples in the tissue gripped between the jaw members. A knife blade which trails the pusher bars cuts the tissue along a line between the staple rows. Examples of such anastomotic stapling instruments are disclosed in U.S. Pat. Nos. 3,499,591 and 4,429,695. In both instances, the pusher bar and knife assembly is operable in a single longitudinal movement, and no provision is made for selection of different staple heights to be produced.

In the use of stapling instruments of the above type, relatively large forces are exerted in clamping the tissue to be fastened between the jaw members, ejecting the staples from the staple cartridge, driving the staples into the gripped tissue, and forming the staples against the anvil. Such forces tend to separate the jaw members vertically and to distort the jaw members laterally, with the result that the consistency of the formed staple height is diminished, or that some staples may completely miss the anvil. This problem is accentuated in the case of a disposable stapling instrument in which relatively lightweight disposable materials are used for the manufacture of the jaw members and other components. Thus, there is a need for a disposable stapling instrument which is capable of accurate alignment of the jaw members while the staple forming operation is performed, and which is more conveniently operable by a reduced amount of force.

In the past, surgical stapling instruments have been designed to produce only one predetermined staple height. Thus, to enable a surgeon to select different staple heights, e.g., to accommodate tissue of different thicknesses, separate stapling instruments each loaded with different staple sizes have been necessary for instances where different staple heights are required. Accordingly, it is highly desirable to provide a surgical instrument capable of selection of two discrete staple heights to allow the stapling instrument to be used with tissue of different thicknesses.

SUMMARY OF INVENTION

The present invention achieves an improved stapling instrument which overcomes the disadvantages of the prior art by incorporating an improved staple actuator mechanism operable by separate control buttons to accomplish the stapling and cutting of the tissue in two stages. The two stage operation of the stapling instrument reduces the maximum force previously required to operate the single stage instruments of the prior art. In addition, the improved actuator mechanism permits one of two different staple heights to be produced by the same instrument. Moreover, the acutator mechanism is designed to stabilize the upper and lower jaw members by providing support along substantially the entire length of the operative portions of both jaw members.

In accordance with the invention, a surgical stapling instrument comprises first and second cooperating jaw members, one of said jaw members including staple carrying means adapted to receive a plurality of staples arranged in at least one row, and said other jaw member including anvil means adapted to form said staples, first means for driving the staples partially from said staple carrying means into tissue gripped between said jaw members to force the staples into the tissue to produce at least one row of unformed staples therein and for cutting the tissue along a line adjacent to said row of unformed staples, and second means for completely ejecting the staples from said staple carrying means and forming the staples against said anvil means to produce at least one row of closed staples adjacent to the line cut in the tissue. In a preferred embodiment, the first and second means are operable separately and sequentially to reduce the force required to actuate the stapling instrument to form the staples and to cut the tissue. Preferably, the stapling instrument includes means for selecting different closed staple heights to be produced when the staples are formed. In the preferred embodiment, the stapling instrument includes means for adjusting the spacing between said jaw members to select one of two predetermined staple heights to be produced when the staples are formed.

Preferably, the invention is embodied in a linear anastomotic stapling instrument which includes elongated upper and lower jaw members for gripping tissue therebetween. A staple cartridge carrying at least two laterally spaced longitudinal rows of staples is mounted on the upper jaw member, and a staple forming anvil is provided on the lower jaw member. A two-stage actuator mechanism is slidably mounted for longitudinal movement relative to the jaw members. In the first stage of operation, the staples are partially ejected from the staple cartridge into the tissue by a first set of staple driving or pinning bars to pin the tissue gripped between the jaw members. The tissue is cut along a line between the staple rows by a knife which immediately follows the staple bars. In the second stage of operation, the staples are completely ejected from the staple cartridge by a second set of staple driving or forming bars which form the staples against the anvil on the lower jaw member.

A preferred embodiment of the stapling instrument includes an actuator assembly in the form of a slidable I-beam structure comprising an elongated knife blade provided with upper and lower longitudinal jaw support members which are slidably received in corresponding passageways formed in the upper and lower jaw members. A first control button is provided for advancing the knife blade and jaw support members longitudinally along the jaw members. With the knife blade advanced forwardly between the jaw members, its longitudinal support members are inserted into the passageways to stabilize the upper and lower jaw members along the entire length of the jaw members by limiting vertical or lateral displacement of the jaw members relative to each other. The upper jaw support member includes a set of staple driving bars provided with cam surfaces for actuating a plurality of staple drivers mounted in the staple cartridge. As the knife blade is advanced, the cam surfaces provided on the staple driving bars successively engage the staple drivers to partially drive the staples from the staple cartridge and to force the staples through the tissue into contact with the anvil on the lower jaw member. Preferably, no staple forming is accomplished as a result of the longitudinal movement of the knife blade and its support members. Thereafter, a second control button is actuated to advance a set of staple forming bars into the staple cartridge to complete the ejection and forming of the staples. The staple forming bars are provided with cam surfaces which successively engage the staple drivers which force the staples into engagement with the anvil to form the staples into conventional B-shaped configurations.

In accordance with a preferred embodiment of the invention, a staple height adjusting sleeve is mounted on the lower jaw support member of the knife blade. This sleeve is elongated and slidably fitted over the lower jaw support member. Depending on the staple height desired, the sleeve can be selectively advanced with the lower jaw support member into the passageway formed in the lower jaw member or not advanced into the passageway. Whether the sleeve is advanced with the lower jaw support member is determined by the lateral position of the first control button prior to its forward advance to actuate the knife blade. The first control button can be set to two different lateral positions to select the desired staple height. With the button in its first, inward lateral position, the sleeve is locked to the lower jaw support member and the knife blade so that the sleeve travels with the lower jaw support member into the corresponding passageway in the lower jaw member. As a result, the upper and lower jaw members are spaced more closely together to achieve a smaller staple height. With the first control button in its second, outward lateral position, the sleeve is free to slide relative to the lower jaw support member. When the first control button is moved forwardly to advance the knife blade, the staple height adjusting sleeve is precluded by frictional forces from entering the passageway in the lower jaw member. As a result, the upper and lower jaw members are spaced farther apart and a larger staple height is achieved.

The invention provides an improved linear gastrointestinal anastomotic stapling instrument which is conveniently operable by a surgeon with less force than required by previous surgical staplers. The stapling instrument achieves accurate and precise rows of staples because the improved actuator assembly provides both longitudinal and lateral support along substantially the entire length of the operative portions of the elongated jaw members which carry the staple cartridge and the anvil during the forming of the staples. The actuator assembly also advantageously allows different staple heights to be selected and produced by the same stapling instrument. In addition, the two-stage operation of the actuator assembly reduces the force required to actuate the stapling instrument to form the staples and cut the tissue in performing an anastomosis.

The present invention also contemplates an improved method of performing a surgical anastomosis which comprises driving a plurality of staples into the tissue to be anastomosed before the tissue is cut to produce at least one row of unformed staples in the tissue, cutting the tissue along a line adjacent to the row of unformed staples, and forming the staples after the tissue is cut to provide at least one row of closed staples adjacent to the line cut in the tissue. The method can be performed by using a surgical stapling instrument including first and second cooperating jaw members, one of the jaw members including a staple cartridge adapted to receive a plurality of staples arranged in at least one row, and the other jaw member including an anvil adapted to form the staples. Preferably, the method comprises clamping the tissue to be anastomosed between the staple cartridge and the anvil on the jaw members, partially ejecting the staples from the staple cartridge into the tissue gripped between the jaw members to force the staples into the tissue before the tissue is cut without forming the staples to produce at least one row of unformed staples in the tissue, cutting the tissue gripped between the jaw members along a line adjacent to the row of unformed staples, and completely ejecting the staples from the staple cartridge and forming the staples against the anvil after the tissue is cut to provide at least one row of closed staples adjacent to the line cut in the tissue. Preferably, the staples are arranged in at least two laterally spaced longitudinal rows and the tissue is cut along a line located between the rows of staples. The invention achieves a method of performing a surgical anastomosis in which the forces required to form the staples and to cut the tissue are minimized.

BRIEF DESCRIPTION OF DRAWINGS

FIG. 1 is an overall perspective view of a linear anastomotic stapling instrument embodying the principles of the present invention;

FIG. 2 is a side elevation, partially disassembled, of the anastomotic stapling instrument;

FIG. 3 is an enlarged, partially cutaway side elevation showing the anastomotic stapling instrument in its assembled configuration;

FIG. 4 is an enlarged top view of the anastomotic stapling instrument;

FIG. 5 is an enlarged vertical section taken along line 5—5 of FIG. 1 through the jaw members of the anastomotic stapling instrument;

FIG. 6 is an enlarged vertical section taken along line 6—6 of FIG. 1 through the handles of the anastomotic stapling instrument;

FIG. 7 is a horizontal section taken along line 7—7 of FIG. 3 showing the anvil carrying jaw member of the anastomotic stapling instrument;

FIG. 8 is a horizontal section taken along line 8—8 of FIG. 3 showing the staple cartridge carrying jaw member of the anastomotic stapling instrument;

FIG. 9 is an enlarged perspective view of an actuator assembly of the stapling instrument;

FIG. 10 is an enlarged perspective view of a staple height adjusting sleeve included in the actuator assembly;

FIG. 11 is a perspective view of a pusher bar mechanism of the stapling instrument;

FIG. 12 illustrates the operation of the actuator assembly to pin the staples into tissue gripped between the jaw members of the stapling instrument;

FIG. 13 illustrates the operation of the pusher bar mechanism to complete the ejection and forming of the staples into the tissue to provide a first predetermined staple height;

FIG. 14 illustrates the operation of the pusher bar mechanism to complete the ejection and shaping of the staples into the tissue to provide a second predetermined staple height;

FIG. 15 is an enlarged plan view of a staple cartridge of the stapling instrument;

FIG. 16 is a vertical section of the anvil and staple cartridge taken along line 16—16 of FIG. 3; and FIG. 17 is a vertical section of the jaw members taken along line 17—17 of FIG. 7.

DETAILED DESCRIPTION OF PREFERRED EMBODIMENT

Referring to FIGS. 1 and 2, the present invention is embodied in a linear anastomotic stapling instrument, generally 20, comprising an upper handle 22 and a lower handle 24 which support upper and lower elongate jaw members 26 and 28, respectively, with each jaw member having an elongated front portion projecting forwardly from its corresponding handle. Preferably, handles 22 and 24 are made of plastic or other lightweight material, while jaw members 26 and 28 are made of stainless steel or other suitable material. Upper handle 22 is provided with a laterally extending cylindrical support knob 30. In addition, upper handle 22 includes a semi-circular notch 32 in its top surface and handle section 24 includes a semi-circular notch 34 in its bottom surface to facilitate the handling and operation of the stapling instrument by a surgeon.

As shown in FIGS. 2 and 6, upper jaw member 26 comprises an elongated, channel-shaped frame having its rearward portion secured between the side walls of upper handle 22 by a plurality of set screws 35. As an alternative, jaw member 26 may be attached by other suitable means to the upper handle. Lower jaw member 28 comprises an elongated, channel-shaped frame pivotally connected to lower handle 24 by a front pivot connection including a transverse pivot pin 36 (FIG. 3) inserted in a depending ear 37 formed at an intermediate position on the bottom of the jaw member. A rear pivot connection is provided between jaw members 26 and 28 by a pivot pin 38 mounted on a pair of upstanding ears 40 (FIG. 17) formed on opposite sides at the rear of jaw member 26. Rear pivot pin 38 is received in a pivot clip 42 including a pair of depending arms mounted at the rear of upper jaw member 26. Preferably, the depending arms of pivot clip 42 are resilient to allow pivot pin 38 to be readily inserted into and removed from the pivot clip. Thus, the rear pivot connection permits the jaw members to be completely disconnected from each other, or remain attached, to facilitate use of the stapling instrument.

Referring to FIG. 17, pivot pin 38 includes a pair of enlarged cylindrical ends located outside of upstanding flanges 40 of lower jaw member 28. A flat base 41 of pivot clip 42 is slidably received within upper jaw member 26. A pair of legs 43 extend laterally from opposite sides at the rear of base 41 of pivot clip 42 into suitable notches provided at the end of upper jaw member 26 to retain the pivot clip in place. The upper jaw member includes a pair of depending side walls 47 which overlap upstanding flanges 40 of lower jaw member 28.

Referring to FIGS. 1 and 3, lower jaw member 28 is seated in a saddle member 44 located at an intermediate position along the lower jaw member adjacent to the front pivot connection. Saddle member 44 is mounted for pivotal movement with lower jaw member 28 relative to handle 24 and is provided with upstanding flanges 45 on its opposite sides. A first spring 46 mounted inside lower handle 24 beneath saddle member 44 normally urges the saddle member and lower jaw member 28 to the inclined position shown in FIG. 2 with the rearward portion of the jaw member extending upwardly from handle 24. A second spring 48 is mounted inside handle 24 adjacent to the rear end of lower jaw member 28 which includes a slot 50 for receiving a bent upper end 52 of spring 48. The second spring 48 serves as a latch to maintain handles 22 and 24 together in a parallel fashion when upper jaw member 26 and lower jaw member 28 are assembled properly. Saddle member 44 receives upper jaw member 26 between its upstanding flanges 45 to maintain the upper and lower jaw members in alignment.

In addition, lower handle 24 includes a pair of laterally spaced hooks 54 projecting upwardly from opposite sides of the front end of the handle. Each hook 54 includes a cam surface 55 which cooperates with a latching pin 56 extending transversely across the interior of upper handle 22 to secure the front ends of handles 22 and 24 together when the stapling instrument is assembled for use. Preferably, latching pin 56 is slidably supported in a pair of vertical grooves 58 (FIG. 2) formed on opposite interior walls of upper handle 22 and is biased upward by a spring 59. As shown in FIG. 3, pivot pin 36 is secured to the bottom of each hook 54.

Referring to FIG. 2, upper jaw member 26 supports a staple cartridge 60 which is adapted to receive a plurality of surgical staples arranged in at least two laterally spaced longitudinal rows. As shown in FIG. 15, the staple cartridge is divided longitudinally by a central, elongated slot 61 which extends from the inner end of the cartridge toward its tapered outer tip 62. Preferably, the staples are received in a plurality of openings 63 formed in staple cartridge 60 which are arranged in two pairs of laterally spaced rows, each pair of rows being disposed on opposite sides of central longitudinal slot 61. As shown in FIG. 15, the staple openings 63 in adjacent rows are staggered to provide more effective stapling of the tissue together when the instrument is operated. The cartridge also includes a pair of longitudinal slots 64 located on opposite sides of elongated central slot 61 and located between the staggered rows of openings 63 on each side of the central slot. Each longitudinal slot 64 extends from the proximal end of cartridge 60 to the tapered tip 62 at its distal end. Preferably, staple cartridge 60 includes a set of projections 66 at its proximal end which are adapted to be snap fitted into channel-shaped jaw member 26 to simplify the manufacture and assembly of the instrument.

As shown in FIG. 12, a plurality of staple drivers 68 are slidably mounted in staple openings 63 for actuating a plurality of staples 65 which are loaded into the cartridge 60. Preferably, each staple driver 68 is designed to simultaneously actuate two staples located in adjacent rows. Thus, a first set of staple drivers 68 is provided for actuating the staples in the staggered rows to the left of central longitudinal slot 61, and a second set of staple drivers 68 is provided for actuating the staples in the pair of adjacent rows located to the right of central longitudinal slot 61.

Referring to FIG. 2, the stapling instrument includes an actuator assembly, generally 70, slidably mounted on upper jaw member 26 which is actuated by a first control button 72. When jaw members 26 and 28 are closed with tissue gripped therebetween, the actuator assembly 70 is slidable longitudinally relative to the jaw members to partially eject the staples from cartridge 60 and force the staples into the tissue gripped between the jaw members and to cut the tissue along a line between the longitudinal rows of staples after the tissue is pinned. Prior to its longitudinal movement, first control button 72 is movable laterally between different control positions to select the desired staple height to be produced.

The stapling instrument includes a second control button 74 which is actuated after the tissue is initially pinned and cut by actuator assembly 70 to operate a staple pusher bar mechanism 75 (FIG. 11) including a pair of elongated staple forming bars 76 having front inclined cam surfaces 78 adapted to completely eject the staples from cartridge 60 and to form the staples into B-shaped configuration. After the stapling of the tissue is completed, control buttons 72 and 74 are retracted to allow jaw members 26 and 28 to pivot apart for removal of the stapled tissue from the jaw members.

Referring to FIG. 7, the front portion of lower jaw member 28 is provided with an anvil, generally 80, comprising a pair of elongated, inwardly extending flanges 82 separated by a central longitudinal slit 84. Each flange is provided with two longitudinal rows of uniformly spaced staple-forming pockets 86 which are adapted to shape the legs of the staples driven from cartridge 60 to form the staples into the conventional B-shaped configuration.

The stapling instrument is designed to achieve precise alignment between staple cartridge 60 and anvil 80 when the instrument is assembled for use. First, as shown in FIGS. 5 and 7, the saddle member 44 includes upwardly projecting flanges 45 which receive upper channel-shaped jaw member 26 therebetween when the upper and lower jaw members are moved together. Second, lower jaw member 28 is provided with a pair of upstanding, spade-like prongs 90 (FIG. 7) formed on the opposite sides of its channel-shaped frame in the vicinity of saddle member 44 which are received in a pair of corresponding slots 92 (FIG. 8) formed in staple cartridge 60. As shown in FIGS. 15 and 16, inclined ramps 94 are provided at the opposite sides of each slot 92 to guide spade-like prongs 90 into the slots.

Referring to FIG. 9, actuator assembly, generally 70, comprises an I-beam structure including a central, elongated knife blade 100 having an inclined front face 102 which is beveled to provide a sharp cutting edge. An upper, elongated flange member 104 extends along the top of knife blade 100 and a lower, elongated flange member 106 extends along the bottom of the knife blade to complete the I-beam structure. As shown in FIGS. 6 and 9, upper I-beam flange member 104 is generally T-shaped in cross-section and provided with a pair of depending longitudinal staple pinning bars 108 which are parallel to and equidistantly spaced from opposite sides of knife blade 100. Each staple pinning bar 108 includes a forwardly projecting, tapered tip 110 (FIG. 9). As shown in FIG. 12, the tip 110 of each staple pinning bar 108 is provided with an inclined cam surface 112 which initially engages staple drivers 68 to force the staples 65 partially from the staple cartridge 60. The remainder of each staple pinning bar 108 has a straight bottom edge 114 which serves to hold the partially ejected staples through the tissue.

As shown in FIG. 6, the upper I-beam flange member 104 includes a pair of elongated, lateral portions 116 located along opposite sides of the upper flange member. Channel-shaped jaw member 26 includes a pair of elongated, inwardly extending shoulders 118 which are spaced apart a sufficient distance to permit the passage of staple pinning bars 108. In addition, shoulders 118 together with the upper interior surface of jaw member 26 define a passageway 120 in which upper flange member 104 is slidably mounted for longitudinal movement relative to the jaw member with lateral portions 116 of the upper flange member sliding on top of shoulders 118 of the upper jaw members.

Referring to FIG. 11, second control button 74 includes a generally rectangular central body 122 from which staple forming bars 76 project forwardly in a spaced, parallel arrangement. The wedge-like tip 78 on one of the staple forming bars 76 is positioned slightly in advance of the wedge-like tip of the other staple forming bar. Second control button 74 is connected by a tapered arm 124 to central body 122 of the pusher bar mechanism. A pair of grooves 126 is formed along opposite sides of central body 122 which provide a pair of flanges 128 at the top of the central body. Grooves 126 are adapted to slidably receive inwardly projecting shoulders 118 (FIG. 6) of upper jaw member 26, while flanges 128 are slidably received in passageway 120 of the upper jaw member. Accordingly, pusher bar mechanism 75 is slidably mounted for longitudinal movement along the upper jaw member.

As shown in FIG. 5 and 16, staple cartridge 60 is mounted within channel-shaped jaw member 26 with its upper surface in abutment with inwardly projecting shoulders 118 of the jaw member. The staple pinning bars 108 (FIG. 6) are slidably received in vertically oriented, elongated slots 64 (FIG. 5) in staple cartridge 60 when staple driving actuator 70 is advanced into the staple cartridge. Slots 64 allow staple pinning bars 108 to engage the staple drivers 68 (FIG. 12) to initially eject the staples 65 partially from the staple cartridge. In addition, staple forming bars 76 (FIG. 13) are also slidably received in the same slots 64 when pusher bar mechanism 75 (FIG. 11) is advanced into the staple cartridge. Slots 64 allow staple forming bars 76 to engage the staple drivers 68 to complete the ejection of the staples 65 from the staple cartridge.

Referring to FIGS. 5 and 6, anvil flanges 82 together with the interior walls of lower jaw member 28 define a passageway 130 for slidably receiving lower I-beam flange 106 of actuator assembly 70. A sleeve 132 (FIG. 10) is slidably disposed on lower I-beam flange 106 and serves as a shim to enable selection of predetermined staple heights to be achieved. Sleeve 132 has a central, longitudinal slit 134 which extends the entire length of the sleeve and divides its top surface into a pair of opposed inwardly extending flanges 136 (FIGS. 6 and 10). As shown in FIG. 10, a pair of upturned projections 138 is provided at the rear end of each flange 136. The projections 138 on each flange are spaced apart to define a notch 140 therebetween.

With the actuator assembly 70 advanced into staple cartridge 60 on the upper jaw member and anvil 80 of the lower jaw member, flange members 104 and 106 determine the spacing between the jaw members. When the sleeve 132 is advanced into anvil 80 with lower flange member 106, jaw members 26 and 28 are set more closely together to achieve a lesser staple height. When sleeve 132 is not advanced into anvil 80 with lower flange member 106, jaws 26 and 28 are spaced farther apart to achieve a greater staple height. In addition, I-beam flange members 104 and 106 serve as upper and lower jaw support members which stabilize jaw members 26 and 28 by providing longitudinal and lateral support along substantially the entire length of the portions of the jaw members at which staple cartridge 60 and anvil 80 are located.

As shown in FIGS. 1 and 2, first control button 72 is generally rectangular in configuration and is slidably mounted on a stem 142 which projects laterally from actuator assembly 70 and extends through the elongated space between handles 22 and 24. As shown in FIG. 6, stem 142 is secured to central blade 100 of the actuator assembly. Button 72 includes a hollow, rectangular extension or sleeve 144 in which stem 142 is slidably received. Stem 142 includes an outwardly projecting finger 143 which extends through a narrow slit formed in button 72. A stop 145 is mounted at the outer end of finger 143 to limit lateral movement of button 72 relative to the actuator assembly. The underside of sleeve 144 includes an inwardly projecting finger 146 which extends toward central blade 100. Finger 146 serves as a latching member which selectively engages central blade 100 and sleeve 132 depending on the lateral position of button 72.

As shown in FIG. 6, with button 72 moved laterally to its outermost position, finger 146 is disengaged from central blade 100 and sleeve 132. With the button in this position, the outer end of stop 145 is flush with the outer surface of the button to provide a visual and tactile indication to the surgeon of the selection of the larger staple height. If button 72 is advanced longitudinally in this position to slide actuator assembly 70 into staple cartridge 60 and anvil 80, sleeve 132, which is disengaged from blade 100, is precluded from longitudinal movement with the actuator assembly by virtue of the friction between sleeve 132 and the interior surfaces of jaw member 28. As a result, sleeve 132 is left behind and only lower I-beam flange 106 is moved into lower passageway 130 beneath anvil flanges 82. Consequently, jaw members 26 and 28 are spaced further apart to accommodate thicker tissue for stapling between the jaw members.

With button 72 moved laterally to its innermost position (FIG. 7), finger 146 is inserted into slot 148 of central blade 100 and is received in the notches 140 between upstanding projections 138 provided on opposite sides of sleeve member 132. As a result, sleeve 132 is latched to blade 100 for longitudinal movement with actuator assembly 70. With button 72 in this position, stop 145 projects outwardly from the outer surface of the button to provide a visual and tactile indication to the surgeon of the selection of the smaller staple height. When button 72 is advanced longitudinally to slide actuator assembly 70 into staple cartridge 60 and anvil 80, sleeve 132 is moved longitudinally with lower I-beam flange 106 into channel 130 underneath anvil flanges 82. Sleeve 132 acts as a shim which serves to move lower jaw member 28 closer to upper jaw member 26 to accommodate thinner tissue for stapling between the jaw members.

As shown in FIG. 9, first control button 72 includes an upstanding tab 150 located on top of sleeve 144. A notch 152 (FIGS. 1 and 6) is formed in the side of upper handle 22 adjacent to the retracted position of control button 72. With control button 72 at this position, tab 150 is movable through notch 152 to permit the control button to be adjusted laterally between its outermost and innermost positions to select the desired staple height to be produced. Thereafter, as first control button 72 is advanced longitudinally, tab 150 must travel along either the inside or the outside of upper handle 22. As shown in FIG. 8, the side wall of handle 22 in front of notch 152 is reduced in thickness to provide a narrow flange 153 along which tab 150 is guided when first control button 72 is moved to its innermost position and advanced toward the staple cartridge. Thus, tab 150 prevents any lateral adjustment of first control button 72 after its longitudinal advance is begun to preclude any change in the selection of the staple height.

Referring to FIG. 12, as actuator assembly 70 is advanced into the staple cartridge, cam surface 112 on each staple pinning bar 108 initially engages a sloped surface 154 on each staple driver 68 to push each staple driver downward and to drive the corresponding staple partially from the staple cartridge. After cam surface 112 completes its action on sloped surface 154 of the staple driver 68, the straight, lower edge 114 of staple pinning bar 108 moves into engagement with a flat upper surface 156 of each staple driver 68 to hold the staple drivers down with the staples in the initial, partially ejected position and the staple legs forced through the tissue. After the tissue is pinned, blade 100 advances to cut the tissue along a line between the longitudinal rows of staples.

When second button 74 is advanced, staple forming bars 76 complete the ejection of staples 65 from the staple cartridge and the forming of the staples against anvil 80. As shown in FIG. 13, cam surface 78 of each staple forming bar 76 acts on sloped surface 154 of each staple driver 68 to push the staple driver downward toward the bottom of the staple receiving slots to completely eject staples 65 from the slots. As a result, the legs of each staple are moved into engagement with the corresponding staple-forming pockets 86 provided in anvil flanges 82 to form the staples into the conventional B-shaped configuration. With lower I-beam flange 106 and sleeve 132 inserted into anvil 80, as shown in FIG. 13, jaw members 26 and 28 are moved closer together and a smaller staple height is achieved. When the lower I-beam flange 106 is inserted into anvil 80 without sleeve 132, as shown in FIG. 14, jaw members 26 and 28 are spaced farther apart and a larger staple height is achieved.

In the operation of stapling instrument 20, the tissue to be stapled and cut must be initially placed between jaw members 26 and 28 and clamped between the jaw members. By pulling handles 22 and 24 apart, lower handle 24 pivots about pin 36 when the pulling force applied to the handle is sufficient to overcome the holding force of latching spring 48. Normally, latching spring 48 holds handle 24 in a position near lower jaw member 28 against the force of leaf spring 46. By pulling lower handle 24 away from upper handle 22, latching spring 48 is disengaged from slot 50 to allow the lower handle to be pivoted about pin 36 by leaf spring 46. When lower handle 24 is at the full extent of its travel or in its full scissored position (FIG. 2), hook 54 slips clear of pin 56 to allow jaw members 26 and 28 to separate. However, the jaw members are still held together at the rear pivot connection provided by pivot pin 38 and pivot clip 42. The pivot clip captures rear pivot pin 38 between its depending arms to provide a temporary hinge which allows the rear end of jaw members 26 and 28 to be pivotally connected together or to be separated as desired. To separate the stapling instrument into two separate halves, the rear portions of jaw members 26 and 28 are pulled apart so that rear pivot pin 38 is snapped out of pivot clip 42.

Next, the tissue to be stapled and cut is placed on jaw members 26 and 28. For example, as shown in FIG. 2, a piece of tubular, intestinal tissue may be slipped onto each jaw member. After the tissue is placed on the jaw members, rear pivot pin 38 and pivot clip 42, if previously disassembled, are reassembled to pivotally connect the jaw members together. When reassembled, rear pivot pin 38 is snapped into place within pivot clip 42. The rear pivot connection initially serves to maintain handles 22 and 24 in a generally parallel relationship.

As shown in FIG. 3, the front portion of lower jaw member 28 which supports anvil 80 is bent upwardly at a slight angle. When jaw members 26 and 28 are moved together, the front, opposed tips of jaw members 26 and 28 initially touch together to provide a distal closure which serves to retain the position of the tissue between the jaw members. Initially, as jaw members 26 and 28 approach each other, the upstanding sides 45 of saddle member 44 straddle upper jaw member 26 to align the jaw members side to side and to position the tissue with respect to the staple cartridge 60 and the anvil 80. Subsequently, as jaw members 26 and 28 move closer together, spade-like prongs 90 on lower jaw member 28 slide into slots 92 in staple cartridge 60. Prongs 90 serve to interlock staple cartridge 60 and anvil 80 to accurately align, both longitudinally and transversely, the staples 65 in cartridge 60 with the pockets 86 in anvil 80.

Next, the tissue is clamped in position by rotating lower handle 24 about pin 36 toward upper handle 22. As a result, cam surface 55 on each hook 54 slides over latching pin 56 until handles 22 and 24 are parallel and leaf spring 48 snaps into place through slot 50 in lower jaw member 28. If a different position on the tissue is desired, lower handle 24 can be moved away from upper handle 22 to disengage latching spring 48. Jaw members 26 and 28 can be opened to release the pressure on the tissue held between the jaw members. After the tissue is repositioned between the jaw members, lower handle 24 can be returned to its closed position to clamp the tissue between the jaw members. There is no limit to the number of times that the stapling instrument can be repositioned on the tissue.

After the tissue is clamped, first control button 72 is actuated to advance actuator assembly 70 longitudinally along jaw members 26 and 28 into staple cartridge 60 and anvil 80. Prior to its longitudinal movement, the lateral position of control button 72 is set either in its innermost lateral position to select a lesser staple height or in its outermost lateral position to select a greater staple height. When button 72 is in its innermost position, stop 145 becomes visible and finger 148 is moved into notches 140 of sleeve member 132 and into the slot 148 provided in blade 100 to latch the sleeve to the lower I-beam flange 106. Alternately, if control button 72 is in its outermost position, sleeve 132 is unlatched and stop 145 is not visible.

As actuator assembly 70 slides longitudinally into anvil 80, sleeve 132 encounters frictional forces which cause the unlatched sleeve to remain stationary so that the lower I-beam flange 106 moves into passageway 130 without the sleeve member. Thus, as shown in FIG. 14, staple cartridge 60 and anvil 80 are spaced farther apart to select a larger staple height. On the other hand, if sleeve 132 is latched to the actuator assembly, the frictional forces are overcome and the sleeve slides underneath anvil flanges 82 with the lower I-beam flange 106 to move anvil 80 closer to staple cartridge 60 to select a shorter staple height. Thus, as shown in FIG. 13, sleeve 132 determines the staple height produced because anvil 80 is moved closer to staple cartridge 60 by a distance equal to the thickness of upper flanges 136 of the sleeve member. In either case, with actuator assembly 70 advanced into staple cartridge 60 and anvil 80, its elongated I-beam structure provides support and alignment along the entire operating length of jaw members 26 and 28. Sleeve 132 is sufficient in length to assist in the support of jaw members 26 and 28 along substantially the entire length of staple cartridge 60 and anvil 80 when it is inserted beneath anvil 80 with the lower I-beam flange 106.

Referring to FIG. 12, as the actuator assembly is advanced, its upper I-beam flange 104 slides into passageway 120 above shoulder 118 while its two wedge-like tips 110 lead staple pinning bars 108 into slots 64 of staple cartridge 60. Cam surface 112 on each staple pinning bar 108 sequentially engages the staple drivers 68 aligned with each longitudinal slot 64. As a result, staple drivers 68 are sequentially pushed downward to partially drive each staple 65 into the tissue gripped between jaw members 26 and 28. As shown in FIG. 12, the staples 65 are partially ejected from the respective openings 63 in staple cartridge 60. The staple legs are forced through the tissue, but the staples are not formed against the anvil. This initial pinning of the staples serves to secure the tissue between jaw members 26 and 28. Subsequently, the tissue is cut between the longitudinal rows of staples as beveled knife edge 102 is advanced through the central, longitudinal slot of the staple cartridge. Thus, the tissue is held firmly between jaw members 26 and 28 while it is cut, and the final staple height is determined.

Next, second control button 74 is actuated to advance staple forming bars 76 longitudinally into staple cartridge 60. The two wedge-type cam surfaces 78 of the staple forming bars 76 move into the same slots 64 in the staple cartridge to push staple drivers 68 downward to complete the ejection of staples 65 from the cartridge and the formation of the staples into B-shaped configuration against anvil flanges 82. One cam surface 78 leads the other slightly to smooth and reduce the peak forces required to operate the instrument.

The force required to advance actuator button 74 is significantly reduced in comparison with other devices because this button accomplishes only one function, i.e., to form the staples. In addition, the sloped surface 154 on each staple driver 68 is oriented at the same angle as the cam surface 78 of each staple shaping bar 76 to provide a flat, sliding contact between these surfaces. After cam surface 78 of staple shaping bar 76 completes its interaction with cam surface 154 of staple driver 68, the widest portion 79 of staple forming bar 76 rides along flat, horizontal surface 156 on top of the staple driver. After this widest point of wedge-like cam 78 moves beyond the staple driver, the formed staples may push the staple drivers upward slightly due to spring-back of the formed staples. However, because of the relief provided by the straight bottom edge of staple forming bar 76, any further friction between the staple drivers and the staple shaping bar due to spring-back of the staples is avoided.

After staples 65 are completely formed, each of the actuator buttons 72 and 74 must be retracted to its original position. If desired, both buttons can be retracted simultaneously. As a result, staple forming bar 76 and the I-beam structure of actuator assembly 70 are removed from the operative portions of jaw members 26 and 28 to permit the jaw members to be separated. Finally, by rotating lower handle 24 away from upper handle 22, hooks 54 are unlatched from pin 56 to allow the handle sections and jaw members to be separated and the stapled tissue to be removed.

The invention in its broader aspects is not limited to the specific details shown and described, and modifications may be made in the structure of the linear anastomotic stapling instrument disclosed without departing from the principles of the present invention.

We claim:

1. A surgical stapling instrument, comprising:
   first and second cooperating jaw members, one of said jaw members including staple carrying means adapted to receive a plurality of staples arranged in at least one row, and said other jaw member including anvil means adapted to form said staples,
   first means for driving the staples partially from said staple carrying means into tissue gripped between said jaw members to force the staples into the tissue to produce at least one row of unformed staples therein and for cutting the tissue along a line adjacent to said row of unformed staples, and
   second means for completely ejecting the staples from said staple carrying means and forming the staples against said anvil means to produce at least one row of closed staples adjacent to the line cut in the tissue.

2. The surgical stapling instrument of claim 1, including:
   means for selecting different closed staple heights to be produced when the staples are formed.

3. The surgical stapling instrument of claim 1, including:
   means for adjusting the spacing between said jaw members to select one of two predetermined staple heights to be produced when the staples are formed.

4. The surgical stapling instrument of claim 1, wherein:
   said first and second means are operable separately and sequentially to reduce the force required to actuate the stapling instrument to form the staples and to cut the tissue.

5. A surgical stapling instrument, comprising:
   first and second cooperating elongate jaw members, one of said jaw members including staple carrying means adapted to receive at least two laterally spaced longitudinal rows of staples, and said other jaw member including anvil means adapted to form said staples,
   first means for driving the staples partially from said staple carrying means into tissue gripped between said jaw members to force the staples into the tissue without forming the staples against said anvil means and for cutting the tissue along a line between said rows of unformed staples,
   second means for completely ejecting the staples from said staple carrying means and forming the staples against said anvil means to produce a pair of laterally spaced rows of closed staples in the tissue on opposite sides of the line cut between said staple rows.

6. The surgical stapling instrument of claim 5, including:
   means for selecting different closed staple heights to be produced when the staples are formed.

7. The surgical stapling instrument of claim 5, including:
   means for adjusting the spacing between said jaw members to select one of two predetermined staple heights to be produced when the staples are formed.

8. The surgical stapling instrument of claim 5, wherein:
said first and second means are operable separately and sequentially to reduce the force required to actuate the stapling instrument to form the staples and to cut the tissue.

9. The surgical stapling instrument of claim 5, wherein said first means comprises:
an elongate actuator assembly slidable longitudinally relative to said jaw members, said assembly including cam means for sequentially driving the staples partially from said staple carrying means to force the staples into the tissue gripped between said jaw members without forming the staples against said anvil means, and knife means for cutting the tissue along a line adjacent to said row of staples.

10. The surgical stapling instrument of claim 9, wherein said second means comprises:
an elongate staple driver slidable longitudinally relative to said jaw members for completely ejecting the staples from said staple carrying means and forming the staples against said anvil means to produce at least one row of closed staples in the tissue.

11. The surgical stapling instrument of claim 10, including:
support means carried by said actuator assembly for aligning and spacing said jaw members apart by a predetermined distance to set the staple height to be produced.

12. The surgical stapling instrument of claim 11, wherein:
said support means is adapted to provide support to said jaw members along substantially the entire length of said staple carrying means and said anvil means while the staples are formed.

13. The surgical stapling instrument of claim 12, wherein:
said support means is adjustable to vary the spacing between said staple carrying means and said anvil means to select one of two different staple heights to be produced.

14. The surgical stapling instrument of claim 5, including:
means for interlocking said staple carrying means and said anvil means to maintain a desired longitudinal and lateral alignment therebetween when the staples are formed.

15. A surgical stapling instrument comprising:
first and second cooperating elongate jaw members, one of said jaw members including a staple cartridge adapted to receive at least two laterally spaced longitudinal rows of staples, and said other jaw member including an anvil adapted to form said staples,
an elongate actuator assembly mounted on one of said jaw members and slidable longitudinally relative to said jaw members, said actuator assembly including cam means for sequentially driving the staples partially from said staple cartridge to force the staples in said longitudinal rows into tissue gripped between said jaw members without forming the staples against said anvil, and knife means for cutting the tissue along a line between said longitudinal staple rows after the unformed staples are forced into the tissue, and
an elongate staple driver mounted on one of said frames and slidable longitudinally relative to said jaw members for completely ejecting the staples from said staple cartridge and forming the staples against said anvil to provide laterally spaced longitudinal rows of closed staples along opposite sides of the line cut in the tissue.

16. The surgical stapling instrument of claim 15, wherein:
said actuator assembly includes support means cooperable with said elongate jaw members and adapted to provide support along substantially the entire length of said staple cartridge and said anvil during the forming of the staples.

17. The surgical stapling instrument of claim 15, wherein said actuator assembly comprises:
an elongated I-beam structure including first and second elongated support members slidable longitudinally into said elongate jaw members to provide support to said jaw members along substantially the entire length of said staple cartridge and said anvil while the staples are formed.

18. The surgical stapling instrument of claim 17, including:
shim means carried by one of said elongated support members, said shim means being selectively movable with said support member into one of said jaw members for adjusting the spacing between said jaw members to determine the staple height to be produced.

19. The surgical stapling instrument of claim 18, wherein:
said shim means comprises an elongated sleeve member slidably received on one of said elongated support members of said actuator assembly.

20. The surgical stapling instrument of claim 15, including:
means for pivotally connecting said jaw members together at remote ends thereof to allow said jaw members to pivot toward and away from each other, and
a saddle member mounted on one of said jaw members at an intermediate position therealong for receiving the other jaw member therein to maintain said jaw members in alignment at said intermediate position.

21. The surgical stapling instrument of claim 15, including:
means for interlocking said staple cartridge and said anvil to maintain the longitudinal and lateral alignment therebetween when the staples are formed.

22. The surgical stapling instrument of claim 21, wherein said interlocking means includes:
one or more upstanding prongs provided on said anvil carrying jaw member adjacent to said anvil, and
one or more slots provided in said staple cartridge for receiving said prongs to align said anvil with said staple cartridge.

23. A surgical stapling instrument, comprising:
first and second cooperating elongate jaw members, one of said jaw members including staple carrying means adapted to receive a plurality of staples arranged in at least one row, and said other jaw member including anvil means adapted to form said staples,
means for driving the staples from said staple carrying means into tissue gripped between said jaw members and forming the staples against said anvil means to produce at least one row of closed staples in the tissue, knife means for cutting the tissue gripped between said jaw members along a line adjacent to said staple row, and support means including elongated support members movable into engagement with each of said jaw members and adapted to provide longitudinal and lateral support to said jaw members along substantially the entire length of said staple carrying means and said anvil means while the staples are formed.

24. The surgical stapling instrument of claim 23, wherein:

said support means includes means for adjusting the spacing between said jaw members to select one of two predetermined staple heights to be produced when the staples are formed.

25. The surgical stapling instrument of claim 23, wherein said driving means comprises:

first means for driving the staples partially from said staple carrying means into tissue gripped between said jaw members to force the staples into the tissue without forming the staples against said anvil means to provide at least one row of unformed staples in the tissue, and second means for completely ejecting the staples from said staple carrying means and forming the staples against said anvil means after the tissue is cut to provide at least one row of closed staples in the tissue adjacent to the line cut by said knife means in the tissue.

26. The surgical stapling instrument of claim 25, wherein:

said first and second means are operable separately and sequentially to reduce the force required to actuate the stapling instrument to form the staples and to cut the tissue.

27. The surgical stapling instrument of claim 23, including:

means for interlocking said staple carrying means and said anvil means to maintain a desired longitudinal and lateral alignment therebetween when the staples are formed.

28. A surgical stapling instrument comprising:

first and second cooperating elongate jaw members, one of said jaw members including a staple cartridge adapted to receive at least two laterally spaced longitudinal rows of staples, and said other jaw member including an anvil adapted to form said staples, means for sequentially driving the staples from said staple cartridge into tissue gripped between said jaw members and forming the staples against said anvil means to produce a pair of laterally spaced longitudinal rows of closed staples in the tissue, knife means for cutting the tissue gripped between said jaw members along a line between said longitudinal staple rows, and support means including elongated support members movable into engagement with each of said elongate jaw members and adapted to provide support along substantially the entire length of said staple cartridge and said anvil during the forming of the staples.

29. The surgical stapling instrument of claim 28, wherein said support means comprises:

an elongated I-beam structure including first and second elongated support members slidable longitudinally into said first and second elongate jaw members, respectively, to provide longitudinal and lateral support to said jaw members along substantially the entire length of said staple cartridge and said anvil while the staples are formed.

30. The surgical stapling instrument of claim 29, including:

shim means carried by one of said elongated support members, said shim means being selectively movable with said support member into one of said jaw members for adjusting the spacing between said jaw members to determine the staple height to be produced.

31. The surgical stapling instrument of claim 30, wherein:

said shim means comprises an elongated sleeve member slidably received on one of said elongated support members of said actuator assembly.

32. The surgical stapling instrument of claim 28, including:

means for pivotally connecting said jaw members together at remote ends thereof to allow said jaw members to pivot toward and away from each other, and a saddle member mounted on one of said jaw members at an intermediate position therealong for receiving the other jaw member therein to maintain said jaw members in alignment at said intermediate position.

33. The surgical stapling instrument of claim 28, including:

means for interlocking said staple cartridge and said anvil to maintain the longitudinal and lateral alignment therebetween when the staples are formed.

34. The surgical stapling instrument of claim 33, wherein said interlocking means includes:

one or more upstanding prongs provided on said anvil carrying jaw member adjacent to said anvil, and one or more slots provided in said staple cartridge for receiving said prongs to align said anvil with said staple cartridge.

35. A method of performing a surgical anastomosis, comprising:

driving a plurality of staples into the tissue to be anastomosed before the tissue is cut to produce at least one row of unformed staples in the tissue, cutting the tissue along a line adjacent to said row of unformed staples, and forming the staples after the tissue is cut to provide at least one row of closed staples adjacent to the line cut in the tissue.

36. The method of claim 35, wherein:

said staples are arranged in at least two laterally spaced rows and said tissue is cut along a line located between said rows of staples.

37. A method of performing an anastomosis using a surgical stapling instrument including first and second cooperating jaw members, one of said jaw members including a staple cartridge adapted to receive a plurality of staples arranged in at least one row, and said other jaw member including an anvil adapted to form said staples, said method comprising:

clamping the tissue to be anastomosed between the staple cartridge and the anvil on the jaw members, partially ejecting the staples from said staple cartridge into the tissue gripped between the jaw members to force the staples into the tissue before the tissue is cut without forming the staples to produce at least one row of unformed staples in the tissue, cutting the tissue gripped between the jaw members along a line adjacent to said row of unformed staples, and completely ejecting the staples from the staple cartridge and forming the staples against the anvil after the tissue is cut to provide at least one row of closed staples adjacent to the line cut in the tissue.

38. The method of claim 37, wherein:

said staples are arranged in at least two laterally spaced longitudinal rows and said tissue is cut along a line located between said rows of staples.

* * * * *

UNITED STATES PATENT AND TRADEMARK OFFICE
CERTIFICATE OF CORRECTION

PATENT NO. : 4,605,001
DATED : August 12, 1986
INVENTOR(S) : Robert G. Rothfuss et al It is certified that error appears in the above—identified patent and that said Letters Patent is hereby corrected as shown below:

In Claim 15, at column 15, line 68, the term "frames" should read --jaw members--.

In Claim 28, at column 17, line 54, the term "means" should be deleted.

Signed and Sealed this

Twenty-ninth Day of December, 1987

Attest:

DONALD J. QUIGG

*Attesting Officer*     *Commissioner of Patents and Trademarks*